United States Patent
Tsai et al.

(10) Patent No.: US 8,367,865 B2
(45) Date of Patent: *Feb. 5, 2013

(54) METHOD AND CATALYST COMPOSITION FOR PREPARING AMIDE

(75) Inventors: Tung-Han Tsai, Taipei (TW); Cheng-Fa Hsieh, Taipei (TW); Chi-Yuan Chen, Taipei (TW)

(73) Assignee: China Petrichemical Development Corporation, Taipei (TW)

( * ) Notice: Subject to any disclaimer, the term of this patent is extended or adjusted under 35 U.S.C. 154(b) by 499 days.

This patent is subject to a terminal disclaimer.

(21) Appl. No.: 12/627,681

(22) Filed: Nov. 30, 2009

(65) Prior Publication Data

US 2011/0077429 A1    Mar. 31, 2011

(30) Foreign Application Priority Data

Sep. 30, 2009  (TW) .............................. 98133115 A

(51) Int. Cl.
   *C07C 231/04*  (2006.01)
   *B01J 31/04*  (2006.01)

(52) U.S. Cl. ........ 562/553; 562/573; 540/534; 540/484; 502/164

(58) Field of Classification Search ............ 562/553, 562/573; 540/534, 484; 502/164

See application file for complete search history.

(56) References Cited

U.S. PATENT DOCUMENTS 6,750,336 B2 * 6/2004 Sato et al. .................... 540/535

FOREIGN PATENT DOCUMENTS

| CN | 1852898 A | 10/2006 |
|---|---|---|
| CN | 1919834 A | 2/2007 |
| WO | 2008/145312 A1 | 12/2008 |

OTHER PUBLICATIONS

WO 2005/028446(English Translation), 2005.*

* cited by examiner

*Primary Examiner* — Shailendra Kumar
(74) *Attorney, Agent, or Firm* — Edwards Wildman Palmer LLP; Peter F. Corless

(57) ABSTRACT

The present invention provides a catalyst composition for preparing an amide, including an amino acid ionic liquid having a cation of formula (I)

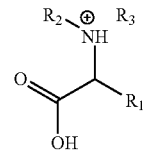

and an anion selected from the group consisting of an inorganic acid group, an organic acid group and a combination thereof, wherein the numbers of the anion and the cation are such that the amino acid ionic liquid is electroneutral; and a Bronsted acid. The present invention also provides a method for preparing an amide in the presence of the catalyst composition, and the method has advantages such as decreasing viscosity of ionic liquid, and increasing conversion rate of ketoximes and selectivity of amides.

9 Claims, No Drawings

METHOD AND CATALYST COMPOSITION FOR PREPARING AMIDE

BACKGROUND OF THE INVENTION

1. Field of the Invention

The present invention relates to a method and a catalyst composition for preparing amides, and more particularly, to a method and a catalyst composition having an ionic liquid and a Bronsted acid for catalyzing ketoximes to produce amides.

2. Description of the Prior Art

Caprolactam is an important raw material in the manufacture of nylon 6 fibers and thin films. Beckman rearrangement of cyclohexanone oxime is an important reaction step in producing caprolactam. Currently, oleum is used as a catalyst for converting cyclohexanone oxime to caprolactam sulfate during Beckman rearrangement, and then ammonia is used for neutralization, so as to obtain caprolactam. While the conversion rate of cyclohexanone oxime is almost 100% and the selectivity for caprolactam is 99%, a large amount of low-valued ammonium sulfate is generated during the reaction, and concentrated sulfuric acid used for catalysis causes problems such as corrosion to the whole equipment and environmental pollution. In the recent years, researches on new production technologies of caprolactam focus on reducing or avoiding the generation of the by-product, ammonium sulfate. Moreover, compared with the gas phase reaction, liquid-phase rearrangement has advantages including moderate reaction conditions, fewer requirements to the equipments, etc., and is advantageous to the reconstruction of the current equipments. As a result, scholars worldwide have put efforts on developing liquid-phase rearrangement, and attained substantial developments and breakthrough. For example, in Chinese Patent No. 1852898A assigned to Sumitomo Chemical Company Ltd. in Japan, an ionic liquid having the sulfonate group is used as a catalyst to give the selectivity of caprolactam up to 99%. In Chinese Patent No. 1919834 assigned to Lanzhou Institute of Chemical Physics in China, an ionic liquid having sulfuryl chloride is used as a catalyst to give the selectivity of caprolactam up to 97.2%. In WO2008/145312A1 assigned to DSM N.V. in Netherlands, an anionic solution having sulfate is used for conversion reaction to give the selectivity of amide up to 99%.

However, in the above-mentioned patents, the acidic ionic liquid is used for catalyzing the conversion reaction, such that if caprolactam is not efficiently separated, there would be a chemical binding between caprolactam and the ionic liquid, and furthermore viscosity of the ionic liquid would be increased, resulting in blocking pipes, which is disadvantageous to fabrication.

Accordingly, there is an urgent need of a catalyst composition for preparing amides which effectively decreases viscosity of an ionic liquid and has high conversion rate of ketoximes and high selectivity of amides.

SUMMARY OF THE INVENTION

The present invention provides catalyst composition for preparing an amide, comprising: an amino acid ionic liquid having a cation of formula (I)

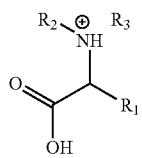

and an anion selected from the group consisting of an inorganic acid group, an organic acid group and a combination thereof, wherein $R_1$ is hydrogen, cycloimino, or $C_{1-8}$alkyl, in which the $C_{1-8}$alkyl is unsubstituted or substituted by a substituent selected from the group consisting of hydroxyl (—OH), carboxyl (—COOH), guanidino ($NH_2C(=NH)NH$—), amino (—$NH_2$), amido (—$CONH_2$), ester group (—COOR, wherein R is $C_{1-8}$alkyl), sulfonate (—$SO_3H$), chlorosulfinyl (ClSO—), hydroxyphenyl, $C_{1-8}$alkylthio, thiol (—SH), $C_{6-10}$aryl and 5- to 10-membered heteroaryl, and $R_2$ and $R_3$ are independently hydrogen or $C_{1-8}$alkyl, in which the $C_1$-$C_8$alkyl is unsubstituted or substituted by a substituent selected from the group consisting of hydroxyl (—OH), carboxyl (—COOH), guanidino ($NH_2C(=NH)NH$—), amino (—$NH_2$), amido (—$CONH_2$), ester group (—COOR, wherein R is $C_{1-8}$alkyl), sulfo (—$SO_3H$), chlorosulfinyl (ClSO—), oxo (=O), hydroxyphenyl, $C_{1-8}$alkylthio, thiol (—SH), $C_{6-10}$aryl and 5- to 10-membered heteroaryl and $C_{6-10}$aryl, and wherein the numbers of the anion and the cation are such that the amino acid ionic liquid is electroneutral; and a Bronsted acid.

The present invention further provides a method for preparing an amide, comprising the steps of: catalyzing Beckman rearrangement of a ketoxime to produce an amide in the presence of an amino acid ionic liquid having a cation of formula (I) and one or more anions selected from the group consisting of inorganic acid ions, organic acid ions and a combination thereof, and in the presence of a Bronsted acid:

wherein $R_1$ is hydrogen, cycloimino, or $C_{1-8}$alkyl, in which the $C_{1-8}$alkyl is unsubstituted or substituted by a substituent selected from the group consisting of hydroxyl (—OH), carboxyl (—COOH), guanidino ($NH_2C(=NH)NH$—), amino (—$NH_2$), amido (—$CONH_2$), ester group (—COOR, wherein R is $C_{1-8}$alkyl), sulfonate (—$SO_3H$), chlorosulfinyl (ClSO—), hydroxyphenyl, $C_{1-8}$alkylthio, thiol (—SH), $C_{6-10}$aryl and 5- to 10-membered heteroaryl, and $R_2$ and $R_3$ are independently hydrogen or $C_{1-8}$alkyl, in which the $C_{1-8}$alkyl is unsubstituted or substituted by a substituent selected from the group consisting of hydroxyl (—OH), carboxyl (—COOH), guanidino ($NH_2C(=NH)NH$—), amino (—$NH_2$), amido (—$CONH_2$), ester group (—COOR, wherein R is $C_{1-8}$alkyl), sulfo (—$SO_3H$), chlorosulfinyl (ClSO—), oxo (=O), hydroxyphenyl, $C_{1-8}$alkylthio, thiol (—SH), $C_{6-10}$aryl and 5- to 10-membered heteroaryl and $C_{6-10}$aryl, and wherein the numbers of the anion and the cation are such that the amino acid ionic liquid is electroneutral.

Compared with conventional processes for catalyzing the Beckman rearrangement by using acidic ionic liquid, the method of the present invention for preparing amides uses a catalyst composition having an ionic liquid and a Bronsted acid, so as to decrease viscosity of the ionic liquid and increase reactivity, conversion rate of ketoximes and selectivity of amides. Therefore, the method of the present invention is suitable for mass production in industry.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention provides catalyst composition for preparing an amide, comprising: an amino acid ionic liquid having a cation of formula (I)

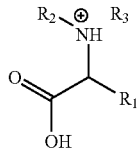

and an anion selected from the group consisting of an inorganic acid group, an organic acid group and a combination thereof, wherein $R_1$ is hydrogen, cycloimino, or $C_{1-8}$alkyl, in which the $C_{1-8}$alkyl is unsubstituted or substituted by a substituent selected from the group consisting of hydroxyl (—OH), carboxyl (—COOH), guanidino ($NH_2C(=NH)NH—$), amino (—$NH_2$), amido (—$CONH_2$), ester group (—COOR, wherein R is $C_{1-8}$alkyl), sulfonate (—$SO_3H$), chlorosulfinyl (ClSO—), hydroxyphenyl, $C_{1-8}$alkylthio, thiol (—SH), $C_{6-10}$aryl and 5- to 10-membered heteroaryl, and $R_2$ and $R_3$ are independently hydrogen or $C_{1-8}$alkyl, in which the $C_1$-$C_8$alkyl is unsubstituted or substituted by a substituent selected from the group consisting of hydroxyl (—OH), carboxyl (—COOH), guanidino ($NH_2C(=NH)NH—$), amino (—$NH_2$), amido (—$CONH_2$), ester group (—COOR, wherein R is $C_{1-8}$alkyl), sulfo (—$SO_3H$), chlorosulfinyl (ClSO—), oxo (=O), hydroxyphenyl, $C_{1-8}$alkylthio, thiol (—SH), $C_{6-10}$aryl and 5- to 10-membered heteroaryl and $C_{6-10}$aryl; and a Bronsted acid.

In a preferred embodiment, $R_1$ is $C_{1-8}$alkyl substituted by carboxyl (—COOH), guanidino ($NH_2C(=NH)NH—$), amino (—$NH_2$), amido (RCONH—) or hydroxyphenyl, and $R_2$ and $R_3$ are independently $C_{1-8}$alkyl.

The term "$C_{1-8}$alkyl" used herein refers to straight, branched, or cyclic alkyl. The $C_{1-8}$alkyl can be, but not limited to, methyl, ethyl, propyl, isopropyl, butyl, sec-butyl, pentyl, hexyl and cyclohexyl, wherein methyl, ethyl, propyl, butyl and pentyl are preferable.

In a preferred embodiment of the present invention, the amino acid ionic liquid is selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof. Preferably, the amino acid ionic liquid is N,N-dimethylglutamic acid sulfate, N,N-dimethylaspartic acid sulfate, N-methylglutamic acid sulfate or N-methylaspartic acid sulfate. It is known from the above that one or more amino acid ionic liquids can be used in the method of the present invention. Specifically, in a preferred embodiment, the amino acid ionic liquid is selected from N,N-dimethylaspartic acid sulfate, N-methylglutamic acid sulfate, N-methylaspartic acid sulfate, N,N-dimethylglutamic acid sulfate, and a combination thereof, and also can be the combination of N-methylaspartic acid sulfate and N-methylglutamic acid sulfate or the combination of N,N-dimethylaspartic acid sulfate, N-methylglutamic acid sulfate and N-methylaspartic acid sulfate.

In the catalyst composition of the present invention, the anion is selected from the group consisting of sulfate, methylsulfonate, trifluoroacetate, hexafluorophosphate, fluoroborate and a combination thereof, wherein sulfate is more preferable.

Generally, the molar ratio of the amino acid ionic liquid and the Bronsted acid is in a range from 1:10 to 10:1, preferably in a range from 1:5 to 5:1, and more preferably in a range from 2:1 to 1:2.

The present invention further provides a method for preparing an amide, comprising the steps of: catalyzing Beckman rearrangement of a ketoxime to produce an amide in the presence of an amino acid ionic liquid having a cation of formula (I) and one or more anions selected from the group consisting of inorganic acid ions, organic acid ions and a combination thereof, and in the presence of a Bronsted acid:

wherein $R_1$ is hydrogen, cycloimino, or $C_{1-8}$alkyl, in which the $C_{1-8}$alkyl is unsubstituted or substituted by a substituent selected from the group consisting of hydroxyl (—OH), carboxyl (—COOH), guanidino ($NH_2C(=NH)NH—$), amino (—$NH_2$), amido (—$CONH_2$), ester group (—COOR, wherein R is $C_{1-8}$alkyl), sulfonate (—$SO_3H$), chlorosulfinyl (ClSO—), hydroxyphenyl, $C_{1-8}$alkylthio, thiol (—SH), $C_{6-10}$aryl and 5- to 10-membered heteroaryl, and $R_2$ and $R_3$ are independently hydrogen or $C_{1-8}$alkyl, in which the $C_{1-8}$alkyl is unsubstituted or substituted by a substituent selected from the group consisting of hydroxyl (—OH), carboxyl (—COOH), guanidino ($NH_2C(=NH)NH—$), amino (—$NH_2$), amido (—$CONH_2$), ester group (—COOR, wherein R is $C_{1-8}$alkyl), sulfo (—$SO_3H$), chlorosulfinyl (ClSO—), oxo (=O), hydroxyphenyl, thiol (—SH), $C_{6-10}$aryl and 5- to 10-membered heteroaryl and $C_{6-10}$aryl, and wherein the numbers of the anion and the cation are such that the amino acid ionic liquid is electroneutral.

In a preferred embodiment, $R_1$ is $C_{1-8}$alkyl substituted by carboxyl (—COOH), guanidino ($NH_2C(=NH)NH—$), amino (—$NH_2$), amido (RCONH—) or hydroxyphenyl, and $R_2$ and $R_3$ are independently $C_{1-8}$alkyl.

In the method of the present invention, the anion is selected from the group consisting of sulfate, methylsulfonate, trifluoroacetate, hexafluorophosphate, fluoroborate and a combination thereof. In a preferred embodiment, the anion is sulfate.

In the present invention, the Bronsted acid can be, but not limited to, sulfuric acid, phosphoric acid, acetic acid, methylsulfonic acid, trifluoromethylsulfonic acid, trifluoroacetic acid, hexafluorophosphoric acid or fluoroboric acid. Further, the Bronsted acid can be a single acid or a mixture of acids. Thus, the Bonsted acid in the present invention is selected from the group consisting of sulfuric acid, phosphoric acid, acetic acid, methylsulfonic acid, trifluoromethylsulfonic acid, trifluoroacetic acid, hexafluorophosphoric acid, fluoroboric acid, and a combination thereof. In a preferred embodiment, the Bronsted acid is sulfuric acid.

Generally, the molar ratio of the amino acid ionic liquid and the Bronsted acid in the present invention is in a range from 1:10 to 10:1, preferably in a range from 1:5 to 5:1, and more preferably in a range from 2:1 to 1:2.

In addition, the ratio of the total molar number of the amino acid ionic liquid and the Bronsted acid to molar number of the ketoxime is in a range from 1:10 to 10:1, preferably in a range from 1:5 to 5:1, and more preferably in a range from 3:1 to 1:3. In the method of the present invention for preparing an amide, the conversion rate of ketoxime is about 100%, and the selectivity of caprolactam is about 98.8%. Hence, it is clear that the Beckman rearrangement of a ketoxime for producing an amide in the presence of the catalyst composition of the present invention has excellent reactivity.

In the method of the present invention, the reaction is performed at a temperature in a range from 60 to 150° C., preferably in a range from 80 to 130° C., and more preferably in a range from 90 to 120° C. Moreover, the reaction is performed for 0.1 to 10 hours, preferably for 0.25 to 4 hours, and more preferably for 0.5 to 1 hour.

In a preferred embodiment, the kemoxime is cyclohexanone oxime. The ketoxime used for preparing the amide in the present invention can be acetone oxime, butanone oxime, benzophenone oxime, acetophenone oxime, cyclopentanone oxime, cyclohexanone oxime, cycloheptanone oxime, cyclooctanone oxime or cyclododecanone oxime.

In the method of the present invention, the amino acid ionic liquid is selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof. Preferably, the amino acid ionic liquid is an isoleucine sulfuric acid-ionic liquid, N,N-dimethylglutamic acid sulfate, N,N-dimethylaspartic acid sulfate, N-methylglutamic acid sulfate or N-methylaspartic acid sulfate. In a preferred embodiment, the amino acid ionic liquid is a glutamic acid sulfuric acid-ionic liquid. Also, one or more amino acid ionic liquids can be used in the method of the present invention.

The following specific embodiments are provided to illustrate the features and effects of the present invention, but not to limit the scope of the present invention.

Embodiments:

The present invention is illustrated by, but not limited to, the following embodiments. Ketoximes and amides were measured by gas chromatography. The conversion rate of ketoximes and selectivity of amides were calculated by the following equations.

Conversion rate (%)=[mole number of reacted ketoxime/mole number of original ketoxime (%)]×100%

Selectivity (%)=[mole number of the resulting amide/mole number of reacted ketoxime (%)]×100%

Embodiments 1-5

As illustrated in Table 1, 0.01 mole of N,N-dimethylglutamic acid sulfate liquid and 0.01 mole of sulfuric acid were added into 250 ml round-bottom flask to form the catalyst composition, and then mixed with 50 ml of toluene and stirred with a magnetic bar. After the temperature of the mixture reached 110° C., the specified amount of ketoxime was added into the mixture, wherein the molar ratio of the total molar number of the ionic liquid and the Bronsted acid to the molar number of the ketoxime was from 5/1 to 5/5 in Embodiments 1-5. The reaction was performed for 0.5 hour, and then the conversion rate of the reactant and the selectivity of the product were measured by gas chromatography and the data were listed in Table 1.

TABLE 1

| Embodiment | Ionic liquid | Sulfuric acid (mol) | Molar ratio* | Rx temp (° C.) | Rx time (hr) | Conversion rate | reactivity |
|---|---|---|---|---|---|---|---|
| 1 | glutamic acid sulfate | 0.01 | 5/1 | 110 | 0.5 | 100% | 97.9% |
| 2 | glutamic acid sulfate | 0.01 | 5/2 | 110 | 0.5 | 100% | 98.8% |
| 3 | glutamic acid sulfate | 0.01 | 5/3 | 110 | 0.5 | 100% | 98.4% |
| 4 | glutamic acid sulfate | 0.01 | 5/4 | 110 | 0.5 | 99.9% | 95.6% |
| 5 | glutamic acid sulfate | 0.01 | 5/5 | 110 | 0.5 | 99.6% | 90.6% |

*molar ratio of the total molar number of the ionic liquid and the Bronsted acid to the molar number of the ketoxime Embodiments 6-10

As illustrated in Table 2, 0.01 mole of N,N-dimethylglutamic acid sulfate liquid and the specified amount of sulfuric acid were added into 250 ml round-bottom flask to form the catalyst composition, and then mixed with 50 ml of toluene and stirred with a magnetic bar. After the temperature of the mixture reached 110° C., ketoxime was added into the mixture, wherein the molar ratio of the total molar number of the ionic liquid and the Bronsted acid to the molar number of the ketoxime was from 5/2. The reaction was performed for 0.5 hour, and then the conversion rate of the reactant and the selectivity of the product were measured by gas chromatography and the data were listed in Table 2.

TABLE 2

| Embodiment | Ionic liquid | Sulfuric acid (mol) | Molar ratio* | Rx temp (° C.) | Rx time (hr) | Conversion rate | reactivity |
|---|---|---|---|---|---|---|---|
| 6 | glutamic acid sulfate | 0.002 | 5/2 | 110 | 0.5 | 100% | 94% |
| 7 | glutamic acid sulfate | 0.005 | 5/2 | 110 | 0.5 | 100% | 94.7% |
| 8 | glutamic acid sulfate | 0.01 | 5/2 | 110 | 0.5 | 100% | 98.8% |
| 9 | glutamic acid sulfate | 0.02 | 5/2 | 110 | 0.5 | 100% | 89.4% |
| 10 | glutamic acid sulfate | 0.05 | 5/2 | 110 | 0.5 | 100% | 83.2% |

*molar ratio of the total molar number of the ionic liquid and the Bronsted acid to the molar number of the ketoxime Comparative Examples 1-5

As illustrated in Table 3, 0.01 mole of N,N-dimethyl-glutamic acid sulfate liquid was added into 250 ml round-bottom flask to form the catalyst composition, and then mixed with 50 ml of toluene and stirred with a magnetic bar. After the temperature of the mixture reached 110° C., the specified amount of ketoxime was added into the mixture, wherein the molar ratio of the total molar number of the ionic liquid and the Bronsted acid to the molar number of the ketoxime was from 5/1 to 5/5 in Comparative examples 1-5. The reaction was performed for 0.5 hour, and then the conversion rate of the reactant and the selectivity of the product were measured by gas chromatography and the data were listed in Table 3.

TABLE 3

| Comparative example | Ionic liquid | Sulfuric acid (mol) | Molar ratio* | Rx temp (° C.) | Rx time (hr) | Conversion rate | reactivity |
|---|---|---|---|---|---|---|---|
| 1 | glutamic acid sulfate | 0 | 5/1 | 110 | 0.5 | 99.8% | 97% |
| 2 | glutamic acid sulfate | 0 | 5/2 | 110 | 0.5 | 99.7% | 89.6% |
| 3 | glutamic acid sulfate | 0 | 5/3 | 110 | 0.5 | 98.9% | 78.2% |
| 4 | glutamic acid sulfate | 0 | 5/4 | 110 | 0.5 | 81.8% | 78.2% |
| 5 | glutamic acid sulfate | 0 | 5/5 | 110 | 0.5 | 61.8% | 74% |

*molar ratio of the ionic liquid to the ketoxime

Accordingly, glutamic acid sulfate-ionic liquid and sulfuric acid were used as the catalyst composition of the present invention for catalyzing ketoxime to produce an amide and achieving high conversion rate of ketoxime and high selectivity of amides. Further, the conversion rate and the selectivity were better when the molar ratio of the ionic liquid to the Bronsted acid is in a range from 5/2 to 5/. Additionally, in the presence of the catalyst composition of the present invention, the amount of ketoxime can be increased without affecting the conversion rate and selectivity, and therefore the present invention facilitate enhance the yield.

Embodiment 11

The viscosity of the catalyst composition before and after the reaction in Embodiment 3 and Comparative example 3 was measured at 60° C., and the data were listed in Table 4.

TABLE 4

| Catalyst composition | Viscosity of ionic liquid before reaction (mm$^2$/s) | Viscosity of ionic liquid after reaction (mm$^2$/s) |
|---|---|---|
| Embodiment 3 | 137.3 | 363.3 |
| Comparative example 3 | 732 | too high to be measured |

As shown in Table 4, the present invention provides a catalyst composition having an ionic liquid and a Bronsted acid for catalyzing a ketoxime to produce an amide in a liquid phase rearrangement condition, thereby decreasing viscosity of the ionic liquid after reaction and enhancing reactivity. In addition, the reaction is performed preferably at 100 to 110° C. for 0.5 to 1 hour.

The reaction system of the present invention is simple, such that no additional cocatalysts are required and no by-products are produced. In the present invention, viscosity of ionic liquid after reaction is decreased, reactivity is enhanced and conversion rate of ketoximes and selectivity of amides are increased, thereby eliminating environmental pollution and saving energy. Thus, the present invention has a promising prospect in industrial applications.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A catalyst composition for preparing an amide, comprising:
   an amino acid ionic liquid selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof; and
   a Bronsted acid.

2. The catalyst composition of claim 1, wherein a molar ratio of the amino acid ionic liquid to the Bronsted acid is in a range from 1:10 to 10:1.

3. The catalyst composition of claim 1, wherein the amino acid ionic liquid is selected from the group consisting of isoleucine sulfuric acid-ionic liquid, N,N-dimethylaspartic acid sulfate, N-glutamic acid sulfate, N,N-dimethylglutamic acid sulfate and a combination thereof.

4. The catalyst composition of claim 2, wherein the Bronsted acid is selected from the group consisting of sulfuric acid, phosphoric acid, acetic acid, methylsulfonic acid, trifluoromethylsulfonic acid, trifluoroacetic acid, hexafluorophosphoric acid, fluoroboric acid, and a combination thereof.

5. A method for preparing an amide, comprising the steps of:
   catalyzing Beckman rearrangement of a ketoxime to produce an amide in the presence of an amino acid ionic liquid selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof and in the presence of a Bronsted acid.

6. The method of claim 5, wherein the Bronsted acid is selected from the group consisting of sulfuric acid, phosphoric acid, acetic acid, methylsulfonic acid, trifluoromethylsulfonic acid, trifluoroacetic acid, hexafluorophosphoric acid, fluoroboric acid, and a combination thereof.

7. The method of claim 5, wherein a molar ratio of the amino acid ionic liquid to the
   Bronsted acid is in a range from 1:10 to 10:1, and a molar ratio of the ketoxime to the total molar number of the amino acid ionic liquid and the Bronsted acid is in a range from 1:10 to 10:1.

8. The method of claim 5, wherein the ketoxime is selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime.

9. The method of claim 5, wherein the Beckman rearrangement is performed at a temperature in a range from 60 to 150°, and performed for 0.1 to 10 hours.

* * * * *